United States Patent [19]

Seppi et al.

[11] Patent Number: 5,335,255
[45] Date of Patent: Aug. 2, 1994

[54] X-RAY SCANNER WITH A SOURCE EMITTING PLURALITY OF FAN BEAMS

[76] Inventors: Edward J. Seppi, 320 Dedalera Dr., Portola Valley, Calif. 94028; John M. Pavkovich, 2945 Alexis Dr., Palo Alto, Calif. 94304; Edward G. Shapiro, 252 Andsbury Ave., Mountain View, Calif. 94043

[21] Appl. No.: 856,231

[22] Filed: Mar. 24, 1992

[51] Int. Cl.$^5$ .................................... G01N 23/00
[52] U.S. Cl. .................................... 378/4; 378/9; 378/5; 378/144; 378/147; 378/64
[58] Field of Search .................... 378/4, 5, 21, 10, 143, 378/144, 146, 147, 8, 901, 64, 65; 382/50

[56] References Cited

U.S. PATENT DOCUMENTS

| | | | |
|---|---|---|---|
| 4,138,611 | 2/1979 | Hounsfield | 378/18 |
| 4,352,021 | 9/1982 | Boyd et al. | 378/12 |
| 4,637,040 | 1/1987 | Sohval et al. | 378/9 |
| 4,669,103 | 5/1987 | Barnea | 378/10 |
| 4,686,695 | 8/1987 | Macovski | 378/5 |
| 4,736,396 | 4/1988 | Boyd et al. | 378/901 |
| 4,984,159 | 1/1991 | Gullberg | 378/901 |
| 4,991,190 | 2/1991 | Mori | 378/9 |
| 5,099,505 | 3/1992 | Seppi et al. | 378/65 |
| 5,117,445 | 5/1992 | Seppi et al. | 378/65 |
| 5,155,365 | 10/1992 | Cann et al. | 378/5 |
| 5,168,532 | 12/1992 | Seppi et al. | 382/50 |

*Primary Examiner*—David P. Porta
*Assistant Examiner*—Kim-Kwok Chu

[57] ABSTRACT

A slow scanning CT Scanner providing slice data simultaneously for a plurality of slices so as to avoid blurring between adjacent slices due to patient movement.

15 Claims, 5 Drawing Sheets

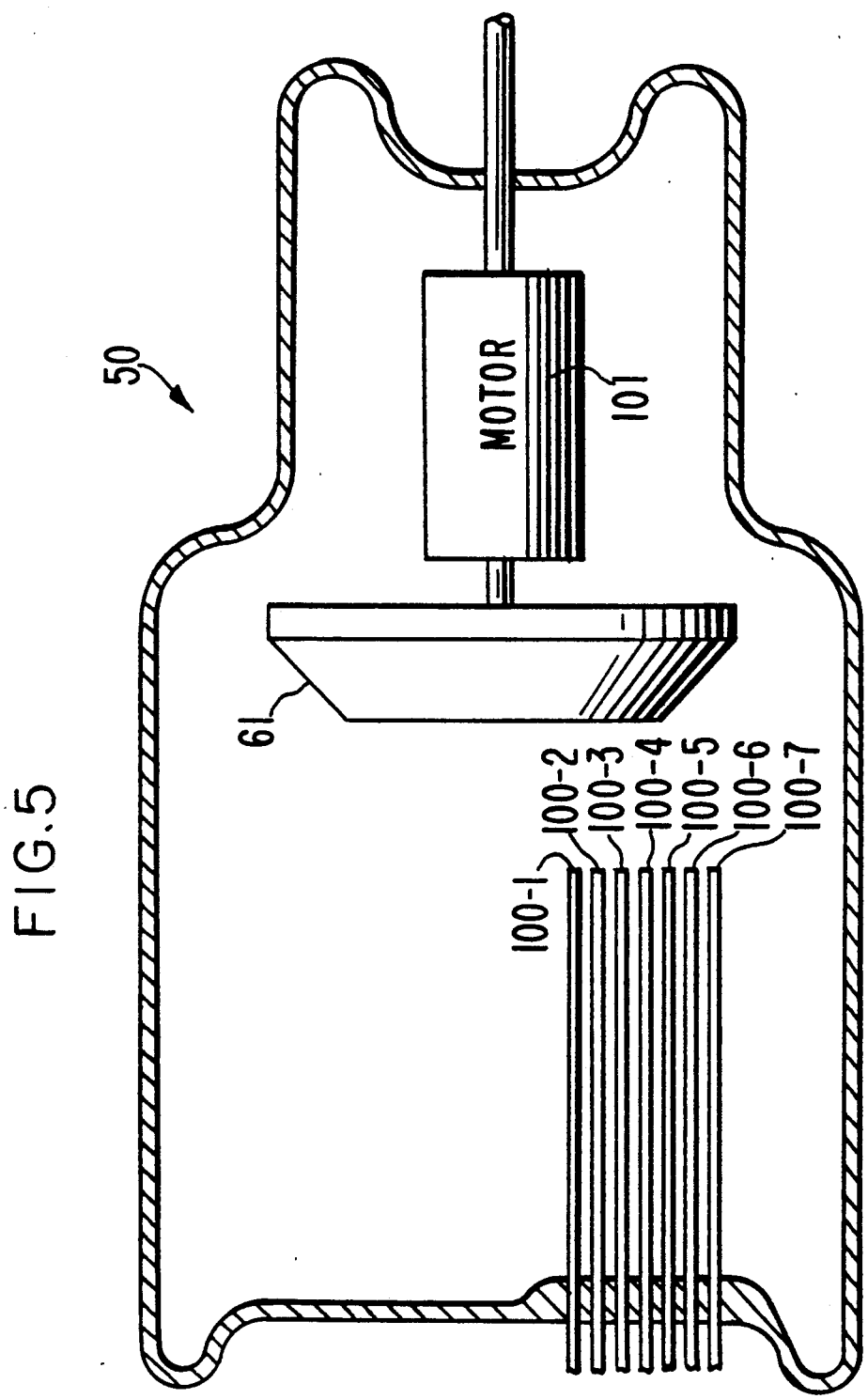

"X-RAY SCANNER WITH A SOURCE EMITTING PLURALITY OF FAN BEAMS"

FIELD OF THE INVENTION

This invention pertains to methods and apparatus for obtaining improved CT images employing apparatus and methods which simulate the geometry of an X-ray therapy machine.

CROSS-REFERENCED APPLICATIONS

Reference is made to the following copending U.S. Patent Applications, owned by the assignee of this invention, which are incorporated herein by reference. This is a continuation-in-part of the following applications:

(1) "Computed Tomography Apparatus using Image Intensifier Detector", Ser. No. 07/547,450, filed Jul. 2, 1990.

(2) "Electronically Enhanced X-ray Detector", Ser. No. 07/547,449, filed Jul. 2, 1990.

(3) "Method for Improving the Dynamic Range of an Imaging System", U.S. Pat. No. 5,168,532.

(4) "Method for Increasing the Accuracy of a Radiation Therapy Apparatus", U.S. Pat. No. 5,099,505.

(5) "Partial Fan Beam Tomographic Apparatus and Data Reconstruction Method", Ser. No. 07/547,596, filed Jul. 2, 1990.

BACKGROUND OF THE INVENTION

Computed tomography scanners (CT) are not well known for providing cross sectional slice X-ray images of a sample. X-rays are made to transit through the sample from various directions and to impinge on a detector so that the detector is responsive to those X-ray photons which are not absorbed. The geometric relationship between the X-ray source and the detector is fixed so that the paired source and detector can be rotated with the sample or patent near the center of rotation while a new set of data is taken at many angular positions around the sample. The data is processed by a high speed computer using known algorithms to provide a reconstruction of the matrix of the density function of the sample with the ability to display this density function in selective planes or slices across the sample.

Diagnosticians study such cross sectional images and can non-invasively evaluate the sample, such as a cancer patient.

In early CT apparatus, the images were frequently blurry, primarily due to the breathing or other movement of the patient during scanning. Several improvements overcome these problems in standard diagnostic CT. Specifically, high power X-ray tubes were developed which made possible higher speed scanning at adequate dose for imaging. This reduced the amount of patient movement between adjacent slices. Additionally, faster and improved algorithms capable of direct fan beam reconstruction without reordering, made real time imaging a meaningful reality. However, these standard diagnostic CT scanners are not optimum for planning radiation therapy for cancer patients. Because high levels of radiation are to be used in treating a cancer patient, it is extremely important that the therapists be able to precisely locate sites of interest for planning and treating. However, the standard diagnostic CT scanner does not configure the patient in exactly the same relationship to the X-ray source as in the radiation therapy machine. Specifically, the position of organs are not the same in the two instruments and this introduces a difficulty in using standard CT Scanners for Radiation Therapy Planning.

Because of this problem, another class of X-ray planning device has become known, called a Simulator. As the term implies, the Simulator is a radiographic/fluoroscopic X-ray device which is shaped and outfitted to simulate the geometry of a radiation therapy treatment machine so that the images formed on the simulator can be interpreted more precisely in terms of the therapy machine. These simulator machines have traditionally been less expensive instruments and did not provide CT scanner capability. As described in the patent applications listed above as CROSS REFERENCED APPLICATIONS, a quality CT scanner capability is now available in simulators as well as in diagnostic CT. However, one major distinction between the CT simulator as compared to the standard diagnostic CT scanner is that the simulator was built to mimic the radiation therapy accelerator and like the radiation therapy accelerator is not capable of high speed scanning. For example, a diagnostic CT scanner X-ray source and detector complete a scan of a 360 degree rotation in about 1-2 seconds. In contrast, the Radiation Therapy Simulator takes about 60 seconds to complete one scan. This is close to the treatment exposure time. This is close to the treatment exposure time. However, because the Simulator scan rate is slower, movement of the patient between and during slices can cause significant deterioration of the data. Also, in order to obtain sufficient patient data for analysis it is not unusual to require as many as ten slices. At a minimum due to patient repositioning and scan processing this requires thirty minutes with the patient required to remain in frequently uncomfortable position for the entire time.

SUMMARY OF THE INVENTION

It is an object of this invention to minimize deterioration effects of patient movement on X-ray scanner data in an X-ray Therapy Simulator.

It is still a further object to increase the rate of data taking in a Radiation Therapy Simulator to shorten total patient time of discomfort during treatment planning.

It is a further object to provide a Radiation Therapy Simulator with improved three dimensional CT having improved point spread correction functions.

It is a feature of this invention to provide n simultaneous fan beams and 2n+1 simultaneously operating array detectors.

It is a still further object to provide this invention as an accessory for use with Radiation Therapy Scanners so that all of the important features and capabilities of those instruments can be retained while relatively inexpensively adding the benefits of volumetric scanning where breathing and other patient motions are correlated across a large number of images.

It is a still further object to provide an instrument and method which enables improved calculation and prediction of dose and dose configuration for radiation therapy.

BRIEF DESCRIPTION OF THE DRAWINGS

FIG. 5 is a drawing of an X-ray tube having multiple filaments.

DETAILED DESCRIPTION OF THE INVENTION

Figure 1:
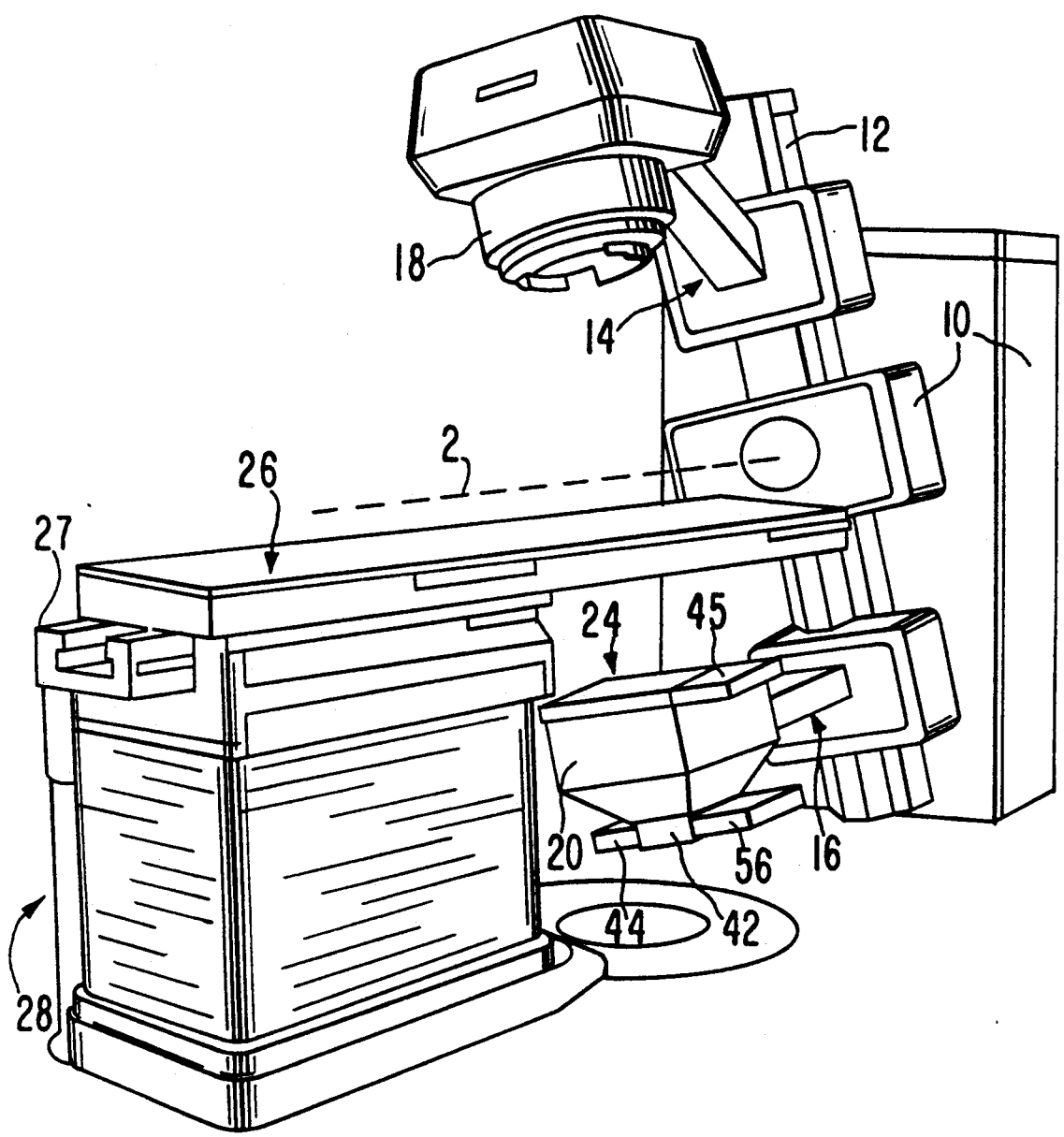
FIG. 1 is prospective view of a Radiation Therapy Simulator.

With reference to FIG. 1, a portion of a prior art Radiation Therapy Simulator, assigned to the same assignee, is described in the References Applications cited above. The gantry is comprised of a drive unit 10 of welded steel fabrication which is bolted to a base 20 which is cast into the floor. In the drive structure 10 is a mechanism for driving the rotating arm 12 with precision around the isocenter axis 2. On the arm 12 are mounted the carriages 14 and 16 for the X-ray head assembly 18 and image assembly 24 including an image intensifier 20, an imaging extension detector 45 mounted slightly obliquely to the image intensifier, a flip mirror assembly 42 for selectively providing the output from the image intensifier to the photodiode linear array 44 or to the television camera 56. In the X-ray head 18 is a high voltage generator in conjunction with a double focus (0.6 mm and 1 mm) X-ray tube containing a lead bladed collimator which can be manually adjusted. Also included in the prior art X-ray head is a motorized cross wire assembly. The treatment couch 26 includes a steel framework supported on a large precision bearing ring mounted into the floor. The frame carries a telescopic ram assembly 28 for the couch 26, and slides 27 for longitudinal movement of the patient as well as a sub chassis for lateral movement.

The above prior art Simulator provided a computerized tomography capability and is more fully shown in FIG. 5 of the copending application Ser. No. 07/547,451 (90-33), referenced above. This prior system, is capable of quality CT scans which are close to the quality of those produced by the very much more expensive and faster diagnostic CT scanners. However, because of the fact that the gantry of the radiation therapy simulator is rotated much more slowly around the patient, i.e. 60 sec vs. 3 second, the breathing and/or movement of the patent causes blurring of the images.

Figure 2:
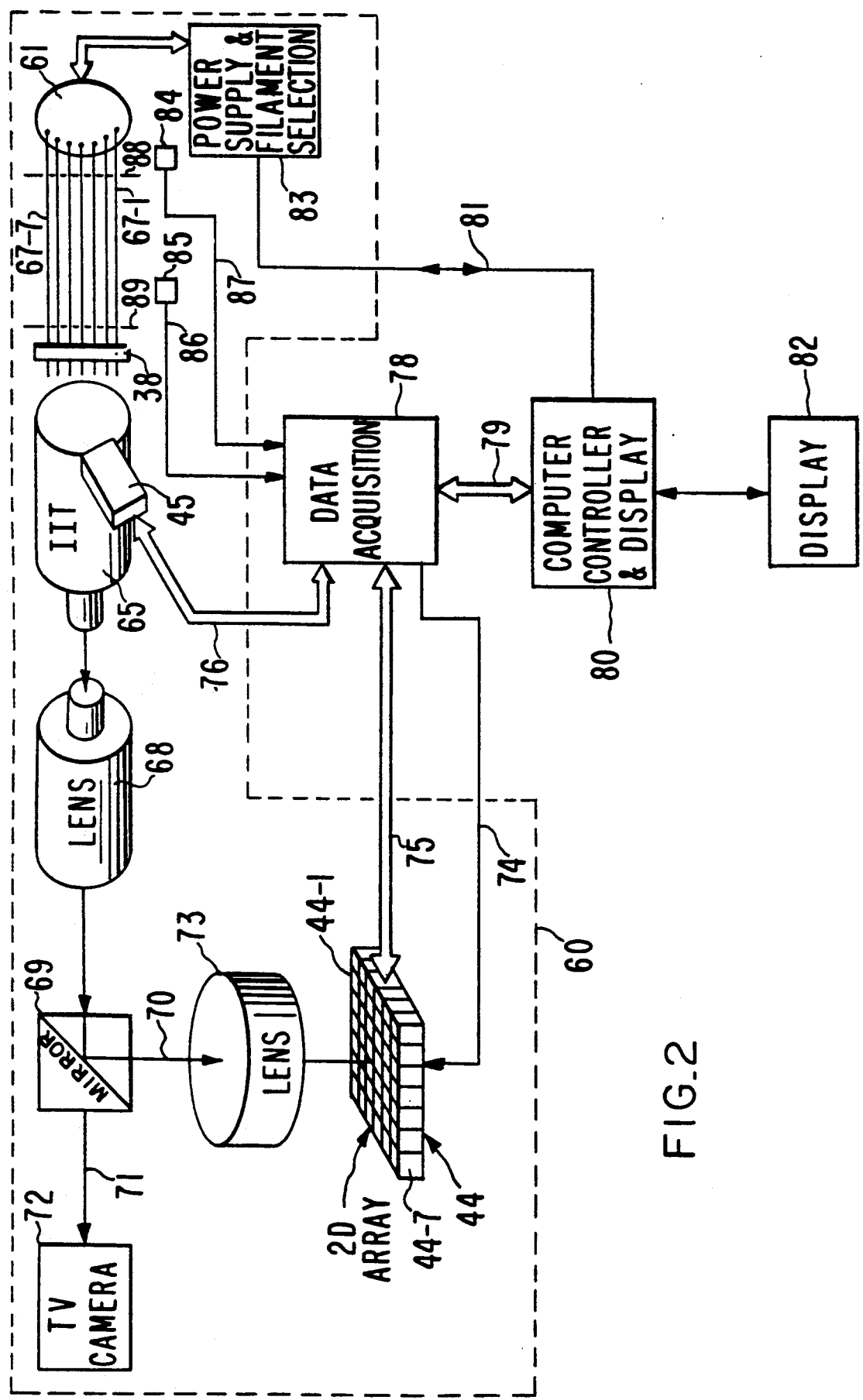
FIG. 2 is a block diagram of the inventive system.

FIG. 2 illustrates schematically the elements of our inventive simulator improvement to minimize the image blurring due to sample or patient movement. We have provided a modified X-ray source tube, 50 in FIG. 5, having a rotating anode 61 having and a large number of filaments, to produce simultaneously X-ray source spots, 61-1 through 61-7, FIG. 2, FIG. 3B and FIG. 4. The X-ray source tube has the same number of separate filaments, FIG. 5, 100-1 though 100-7, as separate source spots. The required close spacing of the filaments in the tube, i.e., 1.5 cm on center, limits the number of filaments. In this embodiment, seven X-ray fan beams are generated simultaneously, 67-1 through 67-7. The fan beams are shaped by precollimator 88, FIG. 2, and post collimator 89 which are described more fully subsequently. The plurality of fan beam 67-1 through 67-7 fall on the image intensifier tube (IIT) 65 and imaging extension 2-D detector array preferably made from a cadmium tungstate scintillator.

In the simulator of copending application Ser. No. 547,450 referenced above, the extension detector was a linear array of 32 discrete detectors of $CdWO_4$ scintillating crystals mounted atop and optically coupled to a UV enhanced silicon photodiode. Our new array of this invention consists of 7×32 discrete detectors. Our array photodiode has an active area of 6 $mm^2$ and the crystal has an active face of 24 $mm^2$. The slice thickness is on the other of 1 cm.

The plural fan beams 67-1 through 67-7 fall on the IIT as explained more fully in the referenced application Ser. No. 547,450. The fan beam in the referenced applications is converted to visible light in the (IIT) and transmitted through lens 68 and right angle mirror 69 to lens 73 and then to a one dimensional photodiode array. In this invention, the photodiode array 44 can be a stack of a plurality of linear arrays 44-1 through 44-7, or it could be a single two dimensional charged coupled detector (CCD). To obtain a spatial resolution of 1 mm on an object, it is necessary to achieve at least 0.9 line pairs/mm. Commercially available CCD arrays with this resolution, such as Texas Instruments TC 215 (1024×1024) or Tektronic (512×512), are available.

A multichannel scanning charge preamplifier, as described in copending Ser. No. 547,450 is used to introduce data from each of the fan beam from the extension detector 45 and multiplex this data with the ITT data from the 2D detectors 44-1 through 44-7.

Preferably, the projection from all the fans are accumulated in computer 80 and simultaneously processed to construct the density function plots for each slice. Algorithms to perform the reconstruction for each fan beam are disclosed in the referenced Parent Application Ser. No. 07/547,596.

To produce images within the same general time as in the prior art, since 7 times the amount of data is being taken, simultaneously, computation speed increases on the order of 7 would be needed. The commercially available array processors such as Intel i 860 have speeds of 4 times that of previous chips, on the order of 80 mega floating point operations per second. By combining N such cards it is possible to increase computational speed by a factor of 4N over the single scan system of copending Reference Application Ser. No. 07/547,596. Alternatively, the data for treatment planning does not necessarily need to be available in real time and the simultaneous collected images can be reconstructed off-line without using the program and the same speed computer as in the system described in Cross Reference Application Ser. No. 07/547,596, filed Jul. 2, 1990.

To enable the operator to view images in real time, or to retain the alternative of operating the system in the single fan beam mode without changing the X-ray tube, a power supply 83, FIG. 2, is provided with the capability to switch off the excitation of the X-ray tube filaments except for the single central filament, 61-4. To retain the same number of pins in the base of the modified X-ray tube, as in a normal two filament X-ray tube, all the filaments of our X-ray Tube are in series and the central filament is tapped on both sides so that it can be excited exclusively. Since the scanning rate for the Simulator is slower than a standard diagnostic X-ray tube, it is only necessary to provide 15 ma current for each filament at 125 KV to obtain the required X-ray dosage. Current X-ray tubes can provide this power level.

Figure 3A:
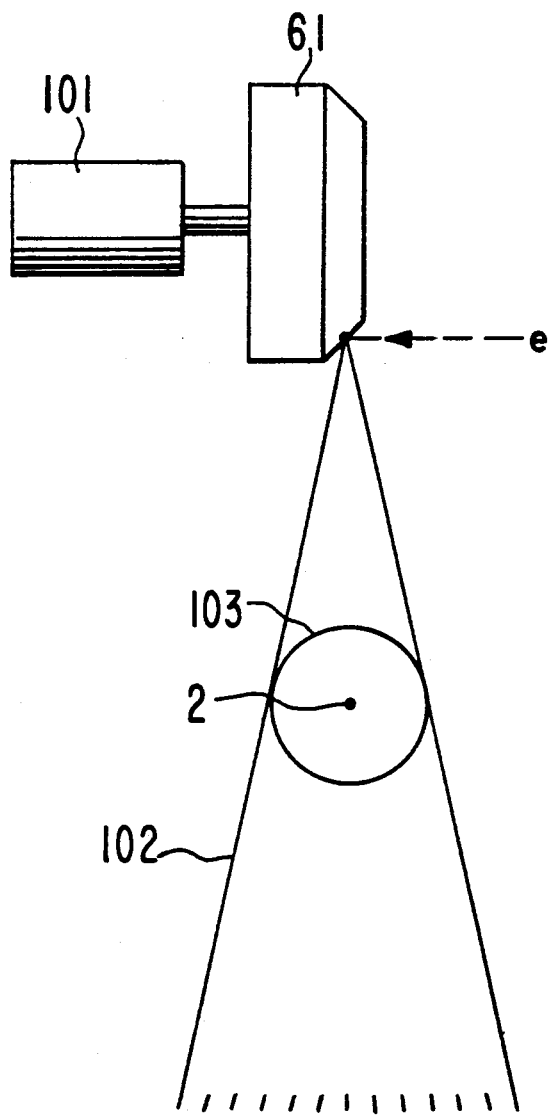
FIG. 3A is a side view of an embodiment of a multiple fan beam X-ray target anode used in this invention.
Figure 3B:
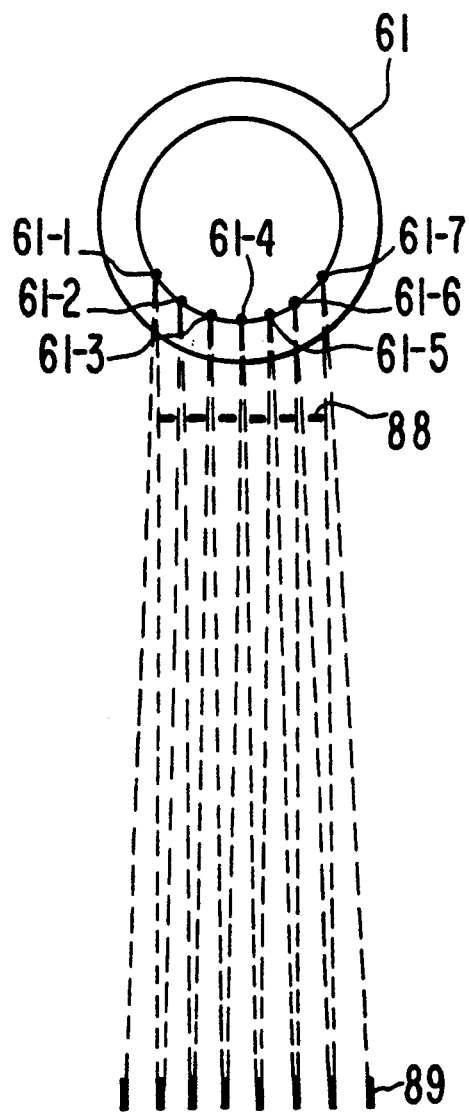
FIG. 3B is a front view of an embodiment of a multiple fan beam X-ray target anode and pre and post collimators.
Figure 4A:
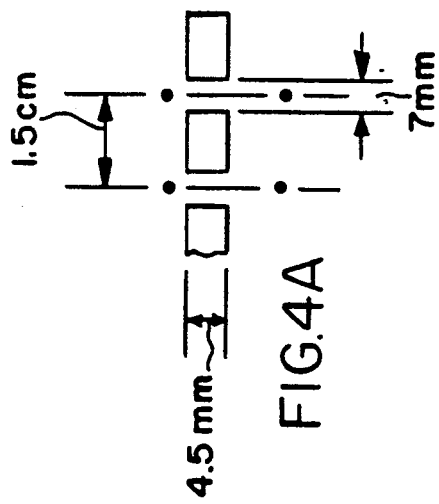
FIG. 4A is a detail of section AA of FIG. 3.
Figure 4B:
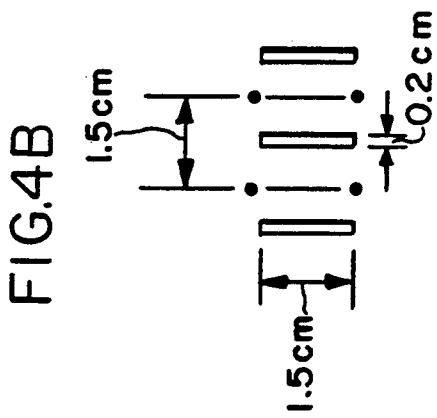
FIG. 4B is a detail of section BB of FIG. 3.
Figure 4:
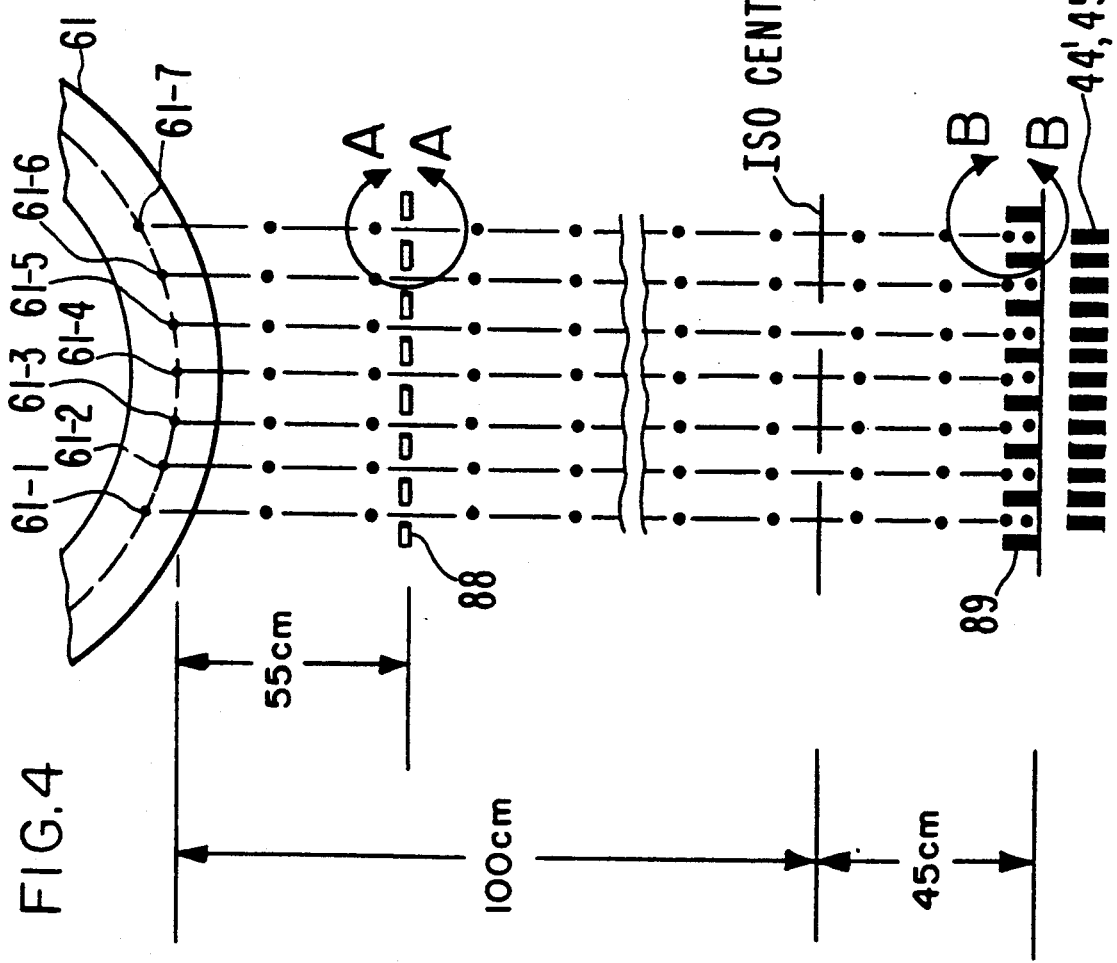
FIG. 4 is a detail of the front view of the relationship of the X-ray target anode and the pre and post collimator.

With reference to FIG. 3A, the X-ray tube motor 101 rotates the tungsten target 61 at high speed, i.e., near 10,000 RPM and the X-ray fan 102 is shown in relation to the isocenter 2 and the normal position for scanning a patient's head 103. FIG. 3B discloses the relationship of the spots 61-1 through 61-7 on the rotating anode target bevel as seen from the front. The lead collimator 88, shown more fully in FIGS. 4 and 4A, is seen to define the width of each of the fans 67-1 through 67-7 which impinge on the patent. The collimator 89 defines the width of the fan beams as they leave the post collimator 89 and enter the detector. FIG. 4, 4A and 4B define the details of the geometry of the relationship between the X-ray target 61 and the collimators 88 and 89. In particular, the central spot 61-4, is 100.0 cm from the isocenter and 55.0 cm from collimator 88. The collimator gaps are on 1.50 cm centers, and each gap is 7 mm. The collimator 89 is also on 1.50 cm centers where the collimator wall portion is 0.2 cm wide.

The post collimator 89 gaps and dimensions and the precollimator 88 gaps and dimensions need to be configurated so that no source spot on the rotating anode has a direct line of sight to any portion of the detector except the portion of the detector which lies on the ray containing the source spot, the center of the corresponding pre collimator gap and the center of the corresponding post collimator gap. Between the collimator 89 and the IIT 65 is an antiscatter focus grid 38 which further rejects X-rays other than line-of-sight X-rays including X-ray scatter from the patient.

Further with respect to FIG. 4, below the collimator 89 is schematically illustrated a series of detector arrays 44' and 45'. As described earlier, the number of detector arrays 44 equaled the number of fan beams. In FIG. 4, we disclose the alternative of employing twice the number of detectors plus 1 times the number of fan beams.

In the copending referenced parent application, Ser. No. 547,799, we describe a crosstalk error as a two dimensional point spread function. This error is seen to arise when a portion of the amplitude received at a detector did not follow the pencil beam path from the source to the detector. This comes from short range scatter and long range scatter (or crosstalk) from X-rays that are along other paths. Although in our earlier patent we provided a correction for the spread function, it was based on theoretical assumption of the model which are not always highly accurate. In this invention, by providing 2N+1 detectors and placing the detectors such that alternative detectors are shielded from the direct X-ray beam by the post collimators 89 we can improve the point spread function correction. Thus, the amplitude received by detectors in the valleys located between the high photon intensity directly receiving detectors corresponds to the crosstalk only. Accordingly, this crosstalk data can be smoothed, interpolated, averaged involving appropriate numerical manipulations to provide a correction for the detector readings from the ridges by subtracting out a position interpolated reading based on the nearby valley position detectors. This provides a much improved point spread correction since it is based on nearby measurement under identical conditions at identical times.

This invention is not intended to be restricted to the particulars of the embodiment disclosed, and it is understood that it can be accomplished by alternate equivalent means. The scope of the invention should be construed by the following claims.

What is claimed is:

1. In a Radiation Therapy Simulator X-ray CT apparatus including radiation therapy simulator gantry means for supporting an X-ray source and a detector and for maintaining said source and detector in a fan beam fixed relationship while said gantry is rotating about an axis in space;
   means to position a sample to be examined by X-rays, said position being between said X-ray source and said detector;
   computer means coupled to said detector for receiving signals proportional to the transmitted X-ray photon intensity of said fan beams of X-rays after said X-rays have traversed through a sample at a plurality of gantry positions about said axis including means to correlate each signal for each fan beam to each said gantry position including means to reconstruct X-ray density cross sectional images of slices of an examined sample by performing fan beam reconstruction computations on said signals, the improvement comprising:
   said X-ray source simultaneously emitting a plurality of parallel fan beams toward said detector;
   said detector includes means for simultaneously receiving said plurality of parallel fan beams; and
   said computer means includes means to compute said X-ray cross sectional density distributions for each of said fan beams.

2. The apparatus of claim 1 wherein said emitting means for simultaneously directing a plurality of N parallel fan beams being an X-ray tube having a rotatable X-ray target anode and n electron guns, said n electron guns for simultaneously launching beams of high energy electrons towards said target anode so that the sources of the X-rays which are emitted from said target anode are spots spatially separated so that each fan beam emitted from said target anode is equally spaced from its next adjacent fan beam.

3. The apparatus of claim 2 wherein the width of each said X-ray fan beam is equal and is defined by a first pre-sample collimator and a second post-sample collimator.

4. The apparatus of claim 3 wherein said first pre-sample collimator and said second pre-sample collimator are configured to preclude direct line of sight between any source spot and any portion of said detector other than the portion of said detector which is aligned to a ray from said spot and which passes through the center point of the gaps in both said pre-collimator and send post-collimator.

5. The apparatus of claim 2 wherein the said detector includes a two dimensional array of visible light detectors.

6. The apparatus of claim 5 wherein said detector includes a two-dimensional visible light array detector, an image intensifier tube (IIT) for converting X-ray photons to visible light, an optical lens means for focusing the visible image of said IIT upon said two-dimensional visible light array detector.

7. The apparatus of claim 5 wherein said two dimensional array comprises a plurality of linear arrays stacked together.

8. The apparatus of claim 7 wherein the number of detector linear arrays equals 2N+1 each said linear array includes two sets of said detectors where a first set of detectors is exposed to fan beam X-rays and a second set of detectors is shielded from said fan beam X-rays by said post-collimators, wherein each detector of said first set alternates with each corresponding detector of said second set.

9. An X-ray CT apparatus comprising:
a gantry having an axis;
an X-ray source and an X-ray detector means, said gantry means for supporting said X-ray source and said X-ray detector in a fan beam relationship and while said gantry is rotating about said axis;
means to position a sample to be examined by X-rays from said source, said position being between said X-ray source and said X-ray detector means;
said X-ray detector means for providing signals, in operation, which are proportional to the transmitted X-ray photon intensity of said beam of X-rays after said X-rays have traversed through a sample at a plurality of gantry positions about said gantry axis;
computer means coupled to said X-ray detector means to correlate each signal for each fan beam to each said gantry position including means to reconstruct X-ray density cross sectional images of slices of an examined sample by performing fan beam reconstruction computations on said signals;
said X-ray source simultaneously emitting a plurality of parallel fan beams toward said X-ray detector means;
said X-ray detector means including means for simultaneously receiving said plurality of parallel fan beams and for providing an output signal indicative of the intensity of said transmitted X-ray photons;
said computer means includes means to compute said X-ray cross sectional density distributions for each of said fan beams.

10. The apparatus of claim 9 wherein said emitting means for simultaneously directing a plurality of N parallel fan beam being an X-ray tube having a rotatable X-ray target anode and n electron guns, said n electron guns for simultaneously launching beams of high energy electrons towards said target anode so that the sources of the X-rays which are emitted from said target anode are spots spatially separated so that each fan beam emitted from said target anode is equally spaced from its next adjacent fan beam.

11. The apparatus of claim 10 wherein the width of each said plurality of said X-ray fan beams is equal and is defined by a first pre sample collimator and a second post sample collimator.

12. The apparatus of claim 11 wherein said X-ray detector means includes a $2N+1$ plurality of detector linear arrays, and where each detector array which is exposed to said fan beam X-rays alternates with each corresponding detector array which is shielded from said fan beam X-rays by said post-collimators.

13. The apparatus of claim 12 where in both the detector array which is exposed and the detector array which is shielded each provide output signals and wherein said detector array which is shielded provide output signals representative of cross talk, the signals derived from both said detector arrays being coupled to said computer, and
means in said computer to use said cross talk representative output signals to generate a point spread correction functions to correct said output signals provided by said exposed detector array.

14. A method for providing an improved correction for point spread function in an X-ray CT apparatus comprising:
shielding alternating detectors of detector linear arrays from receiving direct line of sight X-ray beams, whereby a set of shielded detectors is formed.
simultaneously collecting a first signal from said shielded detectors representative of crosstalk and a second signal from detectors of said detector linear arrays exposed to said X-ray beams and adjacent to said shielded detectors, whereby a set of exposed detectors is formed;
analyzing said collected signals is a computer and providing a correction value of crosstalk for the position of each exposed detector; and
correcting said exposed, detector signals by subtracting said correction value corresponding to the position of said exposed detector.

15. The method of claim 14 wherein said step of providing said corrected value includes smoothing said shielded detector data and interpolating said data to find the value of said crosstalk which corresponds to said position of said exposed detectors.

* * * * *